(12) United States Patent
Rhee et al.

(10) Patent No.: US 6,329,172 B1
(45) Date of Patent: Dec. 11, 2001

(54) ABC TRANSPORTER GENE CLUSTER IN PSEUDOMONAS FLUORESCENS FOR ENHANCED LIPASE SECRETION

(75) Inventors: Joon Shick Rhee, Seoul; Jae Gu Pan; Jung Hoon Ahn, both of Taejon, all of (KR)

(73) Assignee: Korea Advanced Institute of Science and Technology, Taejon (KR)

( * ) Notice: Subject to any disclaimer, the term of this patent is extended or adjusted under 35 U.S.C. 154(b) by 0 days.

(21) Appl. No.: 09/491,772

(22) Filed: Jan. 26, 2000

(30) Foreign Application Priority Data

Mar. 13, 1999 (KR) .............................................. 99-0008512

(51) Int. Cl.[7] .................................................. C12P 21/06
(52) U.S. Cl. .................... 435/69.1; 536/23.1; 536/23.71; 435/6; 435/69.1; 435/320.1; 544/361
(58) Field of Search ............................ 536/23.1, 23.71; 544/361; 435/69.1, 6

(56) References Cited

U.S. PATENT DOCUMENTS

| 5,156,959 | 10/1992 | Abrahmsen et al. ................ 435/69.1 |
| 5,541,087 | 7/1996 | Lo et al. ............................... 435/697 |
| 5,658,755 | 8/1997 | Queener et al. ..................... 435/69.1 |
| 5,665,590 | 9/1997 | Yang ........................................ 435/6 |

OTHER PUBLICATIONS

Walshaw et al., "The general L–amino acid permease of Rhizobium leguminosarum is an ABC uptake system that also influences efflux of solutes", Molecular Microbiology, vol. 21 (6), pp. 1239–1252.*

Ahn et al., Direct Submission Aug. 8, 1998, Biological Sciences, Korea Advanced Institute of Science and Technology (KAIST), 373–1.*

Felmlee, Teresa et al., "Nucleotide Sequence of an *Escherichia coli* Chromosomal Hemolysin," Journal of Bacteriology 94–105 (Jul. 1985).

Glaser, Philippe et al., "Secretion of cyclolysin, the calmodulin–sensitive adenylate cyclase–haemolysin bifunctional protein of *Bordetella pertussis*," The EMBO Journal 3997–4004 (1988).

Highlander, Sarah K. et al., "DNA Sequence of the *Pasteurella haemolytica* Leukotoxin Gene Cluster," Mary Ann Lieber, Inc., Publishers 15–28 (1989).

Mitraki, Anna et al., "Protein Folding Intermediates And Inclusion Body Formation," Bio/Technology 690–697 (Jul. 1989).

Schein, Catherine H., "Production Of Soluble Recombinant Proteins In Bacteria," Bio/Technology 1141–1149.

Létoffé, Sylvie et al., "Protease secretion by *Erwinia chrysantheni*: the specific secretion functions are analogous to those of *Escherichia coli* α–haemolysin," The EMBO Journal 1375–1382 (1990).

Létoffé, Sylvie et al., "Cloning and Expression in *Escherichia coli* of the *Serratia marcescens* Metalloprotease Gene: Secretion of the Protease from *E. coli* in the Presence of the *Erwinia chrysanthemi* Protease Secretion Functions," Journal of Bacteriology 2160–2166 (Apr. 1991).

Tan, Yuping et al., "Cloning, Expression, and Nucleotide Sequence of a Lipase Gene from *Pseudomonas fluorescens* B52, " Applied and Environmental Microbiology 1402–1407 (Apr. 1992).

Johnson, Loreena A. et al, "Degradation of Triglycerides by a Pseudomonad Isolated from Milk: Molecular Analysis of a Lipase–Encoding Gene and Its Expression in *Exherichia coli*," Applied and Environmental Microbiology 1776–1779 (May 1992).

Duong, Franck et al., "Sequence of a cluster of genes controlling synthesis and secretion of alkaline protease in *Pseudomonas aeruginosa*: relationships to other secretory pathways," Gene 47–54 (1992).

Lee, Young P. et al., "Purification and characterization of *Pseudomonas fluorescens* SIK W1 lipase expressed in *Excherichia coli*, " International Journal of Biochemistry and Biophysics 156–164 (1993).

Pugsley, Anthony P., "The Complete General Secretory Pathway in Gram–Negative Bacteria," Microbiological Reviews 50–108 (Mar. 1993).

Akrim, Mohammed et al., "Xcp–mediated protein secretion in *Pseudomonas aeruginosa*: Identification of two additional genes and evidence for regulation of xcp gene expression" Molecular Microbiology 431–443 (Jul. 9, 1993).

Pugsley, Anthony P. et al., "The general secretory pathway of *Klebsiella oxytoca*:no evidence for relocalization or assembly of pilin–like PulG protein into a multiprotein complex," Molecular Microbiology 665–674 (Jul. 29, 1993).

(List continued on next page.)

*Primary Examiner*—Karen Cochrane Carlson
*Assistant Examiner*—Hope A. Robinson
(74) *Attorney, Agent, or Firm*—Darby & Darby

(57) ABSTRACT

The present invention provides ABC transporter gene of *P. fluorescens* encoding a protein which enhances the secretion of foreign proteins extracellularly, a recombinant expression vector containing the transporter gene, a microorganism transformed therewith and a process for preparing foreign proteins which comprises the steps of incubating the transformant, inducing expression of the proteins and leading the proteins to be secreted extracellularly. In accordance with the present invention, foreign proteins can be secreted extracellularly in a simple and efficient manner by employing a secretion system associated with the ABC transporter gene.

18 Claims, 2 Drawing Sheets

OTHER PUBLICATIONS

Fath, Michael J. et al., "ABC Transporters: Bacterial Exporters," Microbiological Reviews 995–1017 (Dec. 1993).

Blight, Mark A. et al., "Heterologous protein secretion and the versatile *Escherichia coli* haemolysin translocator," TIBTECH 450–455 (Nov. 1994).

Hockney, Robert C., "Recent developments in heterologous protein production in *Escherichia coli*," TIBTECH 456–463 (Nov. 1994).

Duong, Frank et al., "The *Pseudomonas fluorescens* lipase has a C–terminal secretion signal and is secreted by a three–component bacterial ABC–exporter system," Molecular Microbiology 1117–1126 (1994).

Akatsuka, Hiroyuki et al., "The Three Genes lipB, lipC, and lipD Involved in the Extracellular Secretion of the *Serratia marcescens* Lipase Which Lacks an N–Terminal Signal Peptide," Journal of Bacteriology 6381–6389 (Nov. 1995).

* cited by examiner

ABC TRANSPORTER GENE CLUSTER IN PSEUDOMONAS FLUORESCENS FOR ENHANCED LIPASE SECRETION

FIELD OF THE INVENTION

The present invention relates to ABC transporter gene cluster, tliDEF, in Pseudomonas fluorescens("*P. fluorescens*"), more specifically, to ABC transporter gene of *P. fluorescens* encoding proteins which enhance the secretion of foreign proteins extracellularly, a recombinant expression vector containing the transporter gene, a microorganism transformed therewith and a process for preparing foreign proteins which comprises the steps of incubating the transformant, inducing expression of the proteins and leading the proteins to be secreted extracellularly.

BACKGROUND OF THE INVENTION

For the last scores of years, various genes from microorganism to human have been isolated and sequenced. In line with the development of biotechnology, foreign proteins have been produced by expressing these genes in host organism such as animal, plant, microorganism, etc. and used it various fields of medicaments, enzymes for biochemical synthesis, food additives and agriculture.

*Escherichia coli*("*E. coli*"), a representative host organism used for introducing gene, has been employed as a research tool for a long time, since it has been throughly investigated to use conveniently. Further many *E. coli* strains for various purposes have been developed so far, which accelerate the use of *E. coli* for the production of useful proteins necessary for industrial purposes and research purposes as well. *E coli* has an advantage of excessive production of desired protein, since it accumulates foreign gene-derived proteins in a level of 20–50% of total proteins. However, there are many cases that proteins are produced not as an active form but as an inactive inclusion body. Production of inclusion body occurred when proteins can not be secreted extracellularly and then excess amount of proteins accumulated in the cell. These proteins are accumulated as an inclusion body before they were refolded to have a biological activity(see: Mitraki et al., Bio/Technology, 7:693(1989)). Many attempts have been made to solve these problems, for examples, change of fermentation condition(see: Schein, Bio/Technology, 7.1141(1989)) or insertion of chaperon preventing inclusion body from being produced(see: Hockney, Trends Biotechnol., 12:456 (1994)).

As an alternative approach, a method for secreting intracellular protein to extracellular medium has been investigated. If tale expressed proteins are secreted extracellularly before the accumulation in the cell, inclusion body is not formed any more. Expressed proteins can be ideally manufactured from microorganism by secreting the proteins in the cell, removing the microorganism from culture media, and obtaining the desired proteins from the media. If the expressed proteins are not secreted to extracellular media, inactive inclusion body is formed, or if the inclusion body is not formed, mechanical, chemical and biochemical methods are required to lyse cells and desired proteins should be purified from many other proteins contained in the cell. This accompanies great loss of expense and loss of proteins. Accordingly, it is of great importance to improve is method for secreting proteins expressed in microorganism to extracellular medium.

In an association with protein secretion, general export pathway(GEP) has been extensively studied, by which N-terminal sequence of protein is recognized by sec protein in the cell to secrete the protein extracellularly(see: Pugsley, Microbiol. Rev., 57:50(1993)) The industrial use of GEP has been considered, since GEP can lead intracellular proteins to attach to cell surface or to be secreted extracellularly(see: U.S. Pat. Nos. 5,156,959; 5,541,087; 5,658,755; and, 5,665, 590). By way of GEP, protein is secreted extracellularly in case of Gram-positive bacteria having only one cell membrane, however, it should pass inner membrane, stay at periplasm and bypass outer membrane in case of Gram-negative bacteria like *E. coli* having two cell membranes. Many proteins($\geq$14) are involved in the export through only outer membrane, which in turn, reveals a serious problem that secretion efficiency is relatively low(see: Akrim et al., Mol. Microbiol., 10:431(1993); Pugsley and Possot, Mol. Microbiol., 10:665(1993)).

Another pathway, mediated by ABC transporter(ATP binding cassette transporter), has been also known in the art, where ATP is hydrolyzed to secrete protein(see: Fath and Kolter, Microbiol. Rev., 57:995(1993)). Protein thus secreted has a C-terminal targeting signal, which is recognized by ABC transporter, to secret the protein extracellularly. Protein secretion is carried out by the aid of ABC transporter protein located at cell membrane and proteins of both Gram-positive and Gram-negative. bacteria can pass cell membrane at once. That is, in case of Gram-negative bacteria, secretory protein makes inner membrane fuse partly with outer membrane, which allows the protein to pass 2 membranes at the same time. Accordingly, the secretion pathway based on ABC transporter is more efficient in Gram-negative bacteria such as *E. coli*.

Until now, many ABC transporters have been successively known in the art, those associated with cyclolysin (see: Glaser et al., EMBO J., 7:3997(1988)), leucotoxin(see: Highlander et al., DNA, 8:15(1989)), protease and lipase, since a secretion system associated with α-hemolysin(see: Felmlee et al., J. Bacteriol., 163:94(1985)) was discovered in *E. coli*. Especially, ABC transporter secreting α-hemolysin has been extensively studied and it is proposed as a universal secretory system, based on the results that other proteins can be secreted by C-terminal targeting signal (see: Blight and Holland, Trends Biotechnol., 12:450(1994) In this connection, ABC transporters cloned from Pseudomonas sp., Erwinia sp. and Serratia sp., are practically applied for the secretion of protease extracellularly (see: Duong et al., Gene, 121:47(1992); Letoffe et al., EMBO J., 9:1375(1990); Letoffe et al., T. Bacterol., 173:2160(1991)). However, little attraction has been, paid to ABC transporter for secreting lipase.

So far, two kinds of ABC transporters secreting, lipase extracellularly have been reported in the art: First, a gene secreting lipase was cloned from *Serratia marcescens*(see: Akatsuka et al., J. Bacteriol., 177:6381(1995)); second, ABC transporter secreting protease from *P. aeruginosa* was revealed to secrete lipase of *P. fluorescens*(see: Duong et al., Mol. Microbiol., 11; 1117(1994)). Naturally, ABC transporter has not been practically applied in industry since only the ABC transporters from *Serratia marcescens* and protease from *P. fluorescens* are available to secrete lipase. In addition, ABC transporter for lipase secretion has not been found in *P. fluorescens*, though the lipase from the microorganism was cloned in many research groups(see: Lee et al, Biochim. Biophys. Acta., 1169:156(1993); Tan et al., Appl. Environ. Microbiol., 58:1402(1992); John et al., Appl. Environ Microbiol., 58:1776(1992)).

Accordinqly, there are strong reasons for exploring ABC transporter gene from *P. fluorescens*, and to develop a novel process for preparing foreign proteins by ABC transporter in a simple and efficient manner.

SUMMARY OF THE INVENTION

The present inventors first cloned a gene encoding ABC transporter from *P. fluorescens*, and constructed an expression vector containing the said gene and lipase or protease coding gene which can be expressed in Gram-negative bacteria such as *E. coli* and Pseudomonas sp., to secrete the lipase or protease proteins. As a result, it was found that these proteins can be produced and accumulated in extracellular medium with a high efficiency. Since the ABC transporter enhancing the secretion of foreign proteins functions at a low temperature of below 25° C., it can prevent inclusion body formation, which allows universal use of the ABC transporter for industrial purposes.

The first object of the invention is, therefore, to provide ABC transporter gene from *P. fluoresens* which enhances the secretion of foreign proteins to extracellular medium.

The second object of the invention is to provide an expression vector containing the ABC transporter gene which is designed to secrete foreign proteins extracellularly.

The third object of the invention is to provide recombinant expression vectors which are constructed to express and secrete foreign proteins extracellularly by ABC transporter.

The fourth object of the invention is to provide a transformant harboring the ABC transporter expression vector.

The fifth object of the invention is to provide a process for preparing foreign proteins by secreting the proteins expressed in the transformant extracellularly by ABC transporter.

BRIEF DESCRIPTION OF THE DRAWINGS

The above and the other objects and features of the present invention will become apparent from the following description given in conjunction with the accompanying drawings, in which.

DETAILED DESCRIPTION OF THE INVENTION

Figure 1:
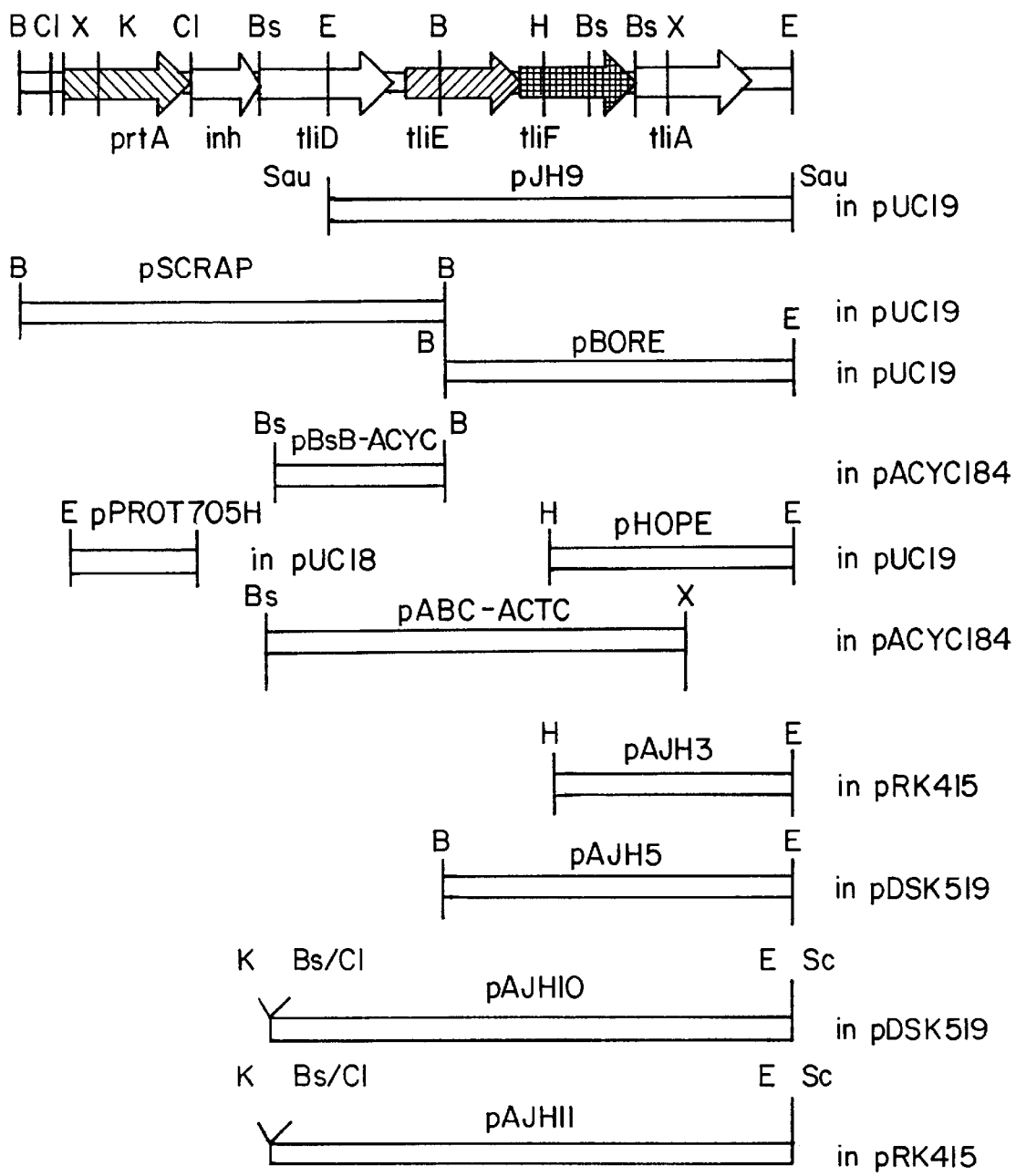
FIG. 1 shows a gene arrangement of ABC; transporter on *Pseudomonas; fluorescens* DNA and restriction maps of various plasmids containing these genes.

In describing the present invention, the term ABC transporter gene' is employed to mean a gene encoding ABC transporter which promotes secretion of foreign proteins expressed in a microorganism extracellularly. ABC transporter gene from *P. fluorescens* is further illustrated in detail.

ABC transporter gene of the present invention was cloned from total DNA of *P. fluorescens*. The ABC transporter gene can be cloned in *P. fluorescens* SIK W1(KCTC 2689P), *P. fluorescens* B52, *P. fluorescens* LS107d2, *P. fluorescens* (*Serratia marcescens* Sr41) or *P. fluorescens* FT(JP 1997224679-A 1 Sep. 02, 1997) which produce lipase or protease.

Plasmid vectors which are replicable in transformants and have resistance to antibiotics such as (ampicilin, chloramphenicol, kanamycin or tetracycline, and have promoter such as lac, tac, trp or PCm, can be used to clone the ABC transporter gene. Among these vectors, pUC18, pUC19(see; Yanisch-Perron et al., Gene, 33:103(1985)) or pBluescript(Stratagene, USA) may be used as high-copy-number plasmids, and pBR322(see: Rodriguez et al., Gene, 2:95(1977)), or pACYC184(see: Chang and Cohen, J. Bacteriol., 134:1141(1978)) may be used as low-copy number plasmids. Since the origin of replication of pUC18, pUC19 or pBluescript is different from pACYC184, replication and maintenance of high-copy-number plasmids are possible when these plasmids are introduced into microorganism with pACYC184.

*E. coli* can be usually used as a host for recombination of the plasmid vectors and analysis of DNA sequence as well, inter alia, *E. coli* XL1-Blue, JM109 and DH5 which are widely distributed and commercially available, are preferred. These *E. coli* can be used to express interested genes, and Pseudomonas sp. Such as *P. fluorescens, P. putida, P. aeruginosa* and *P. fragi* can be also used for the same purpose. According to the present invention, a gene encoding lipase was first screened to clone ABC transporter gene, since the ABC transporter gene is frequently located adjacent to the genes encoding secretory proteins: Total DNA of *P. fluorescens* was digested with restriction enzymes, and DNAs of proper size was collected and inserted into vector to construct genomic library for cloning of lipase gene. If the genomic library is spread on a medium confirming lipase activity, like LAT media containing LB, tributyrin and ampicilin, active halos appear in *E. coli* with lipase gene. Consequently, lipase gene can be selected. After cloning of lipase gene, upstream and downstream DNA sequence of lipase gene was analyzed to confirm whether ABC transporter gene was contained or not.

If the ABC transporter gene had existed, it was investigated whether all components of ABC transporter gene are contained or not. If ABC transporter gene cluster had not been contained in cloned vector, other components were selected by Southern hybridization: Total DNA was digested with EcoRI, HindIII, BamHI, KpnI, SalI, SacI, etc., electrophoresed, and hybridized band was eluted with probe homologous to a part of ABC transporter gene. The extract was inserted into a vector, introduced into *E. coli* and colony hybridization was performed to screen *E. coil* harboring recombinant vector containing desired gene. Recombinant vector containing the other region of ABC transporter gene was obtained by isolating vector from *E. coli* selected by colony hybridization. ABC transporter gene(tliDEF), protease, protease inhibitor and lipase gene(tliA) were cloned from *P. fluorescens*. ABC transporter gene was a double helix DNA of 4540 bp long composed of 3 open reading frame(ORF), and protease, protease inhibitor and lipase gene of *P. fluorescens* was located upstream and downstream of ABC transporter gene, respectively.

After cloning of ABC transporter gene as described aboves, a transformant which secretes foreign protein to extracellular medium was constructed by introducing both foreign protein encoding gene and tliDEF into Gram-negative bacteria such as *E. coli* and Pseudomonas sp. Two kinds of transformants may be constructed as follows: The first one is constructed by transforming with one expression vector containing genes encoding foreign protein and ABC transporter gene, and the other one is constructed by transforming with two different recombinant expression vectors containing the said genes in a separate manner.

In the former case, it has an advantage of using an antibiotic to maintain expression vector. However, the expression of foreign protein gene and ABC transporter gene can not be controlled independently, since the said two genes are regulated by one promoter. In the latter case, though the expression of each recombinant vector can be regulated independently, two antibiotics are essentially required. Since ABC transporter should be located in cell membrane to secrete foreign proteins to extracellular medium, expression and secretion can be maximized effectively if the expression of ABC transporter gene is carried out constitutively and the expression of foreign protein gene is induced at the initial stage of log phase. In accordance with the present invention, a recombinant vector pABC-ACYC containing ABC transporter gene of *P. fluorescens*, pHOPE containing lipase gene, and pPROT705 containing protease gene were constructed, respectively, and found that lipase or protease was secreted extracellularly by transforming a microorganism with two recombinant expression vectors. A transformant was constructed by transforming *E. coli* XL1-Blue with ABC transporter-expressing vector of pABC-ACYC. The transformed *E. coli* was named *Escherichia coli* XL1-Blue/pABC-ACYC', and deposited with the Korean Collection for Type Cultures(KCTC, #52, Oun-dong, Yusong-ku, Taejon 305–333, Republic of Korea) an international depository authority, on Mar. 9, 1999 as accession numbers of KCTC 0586BP.

Incubation is carried out at below 27° C., preferably 15–27° C., more preferably 18–25° C. Expression vector containing foreign protein gene was introduced into *E. Coli* or Pseudomonas and incubated at low temperature, since ABC transporter gene of *P. fluorescens* functions at low temperature and secrete foreign proteins optimally. Moreover, incubation at low temperature prevents the formation of inclusion body and induces the production and secretion of foreign proteins. This system has an advantage of producing foreign protein with high efficiency, by introducing expression vector into low temperature-resistant microorganism such as *P. fluorescens*. Further, high expression of foreign protein or ABC transporter can be realized by adding an inducer of IPTG when the recombinant microorganism containing induction vector reached log phase.

Proteins may be isolated from medium by saltinq out employing highly concentrated salt solution or detergents, use of ion chromatography, protein precipitator or combination thereof. Lipase isolated from nutrient broth may be used immediately after centrifugation, or concentrated through ultrafiltration, lyophilized and solidified. Lipase of *P. fluorescens* can be easily isolated by inactivating other proteins at a high temperature since it is resistant to heat treatment.

The present invention is further illustrated in the following examples, which should not be taken to limit the scope of the invention. In particular, the ABC transporter gene of the invention covers a DNA sequence from *P. fluorescens* disclosed herein and its functional equivalents as well which are prepared by insertion mutation, chemical mutation, random mutation, or PCR technique aided mutation.

EXAMPLE 1
Cloning of ABC Transporter Gene

EXAMPLE 1—1:
Isolation of Total DNA Containing Lipase and ABC Transporter Genes

In order to screen ABC transporter gene, total DNA was isolated from *P. fluorescens* as follows: 100 ml of nutrient broth was inoculated with *P. fluorescens* SIK W1 (KCTC 2689P) and incubated at 25° C. for about 24 hours. The culture was centrifuged, and suspended with 15 ml of saline-EDTA buffer(containing 0.15M NaCl and 0.1M EDTA). After incubating at 37° C. for 30 minutes with 3 mg lysozyme, cells were shaked vigorously and lysed by adding 0.2 ml of 25% SDS(sodium dodecylsulfate). Foreign proteins and impurities were extracted 5 times with 10 mM Tris-buffered phenol and extracted 2 times with phenol-chloroform(1:1, v/v) solution. DNA was collected by swirling glass rod after adding 1/10(v/v) of 3M sodium acetate and 2 volumes of ethanol to the resultant solution. Total DNA was washed with 70% (v/v) ethanol, air-dried and resuspended in TE buffer(10 mM Tris, 1 mM EDTA, pH 8.0).

EXAMPLE 1-2
Cloning of Lipase Gene

Since the ABC transporter gene is frequently located adjacent to the genes encoding secreted proteins in DNA of microorganism, a gene encoding lipase, to clone ABC transporter gene, was screened as follows: Total DNA collected in Example 1-1 was partially digested with restriction enzyme Sau3AI, and the fragments of about 4 to 20 kb were isolated by sucrose gradient centrifugation. This DNA fragments are digested with BamHI and ligated to pUC19 vector dephosphorylated with calf intestinal phosphatase. Recombinant plasmids containing various DNA fragments were used to transform *E. Coli* and genomic library was constructed. Genomic library thus constructed was screened by plating on LAT medium which is used to measure lipase activity, and 12 colonies showing lipase activity were selected. Since clear halo may appear on the LAT plate by the activity of esterase, 12 colonies were placed on ROM plate(nutrient broth, 0.001% Rhodamin-B, 1.0% olive oil and 1.5% agar) to confirm lipase activity, and only one out of the 12 colonies was revealed to possess lipase activity. Recombinant vector isolated from this colony confirmed that 10.2 kb DNA was inserted into the vector and a gene encoding lipase was located in the middle of inserted DNA. This recombinant vector was named 'pJH9' (sec: FIG. 1).

EXAMPLE 1-3
Cloning of ABC Transporter Gene for Lipase Secretion

Upstream and downstream of lipase gene in pJH9 was sequenced and it was determined that: though the ABC transporter gene secreting lipase was located upstream region, only some components of the ABC transporter gene were contained in pJH9. Therefore, Southern hybridization was carried out to find other component of the ABC transporter gene: Total DNA of *P. fluorescens* obtained in Example 1—1 was digested with HindIII, BamHI, and KpnI, respectively, and electrophoresed on 1% agarose gel and then transferred onto a nitrocellulose membrane by electroblot. Probe homologous to 1.3 kb fragment produced by HindIII-BamHI digestion of pJH9 was synthesized, and hybridized with nitrocellulose membrane. As a result, hybridized bands were detected in HindIII- and BamHI-digested chromosomal DNA among DNA of *P. fluorescens* ($\geq$13 kb for HindIII, 4.5 kb for BamHI). The 4.5 kb BamHI DNA fragments were eluted and ligated into BamHI-digested pUC19, and the cloned plasmid were transformed into *E. coli*, and plated on LB plate, then colony hybridization was performed to select transformant containing ABC transporter gene, and 2 colonies containing the same plasmids were finally selected. Cleavage map of insert revealed that 3' region of the insert was overlapped with the 5' region of the insert in pJH9. This recombinant vector was named 'pSCRAP' (see: FIG. 1).

EXAMPLE 2
Analysis of Cloned Gene

To analyze DNA sequence of cloned recombinant vectors (i.e., pJH9 and pSCRAP), the vectors were digested with various restriction enzymes on the basis of cleavage map of 2 vectors, and the fragments were subcloned into M13mp18 and M13mp19. DNA sequence was analyzed with ABI PRISM BigDye primer cycle-sequencing kit(Perkin-Elmer, USA) by using AmpliTaq DNA polymerase, where synthetic nucleotides were also employed for sequencing each side of 2 strands of DNA. Analysis of 8.5 kb DNA revealed that this DNA contained 6 open rending frames and 3 among them were associated with lipase ABC transporter gene. Genes encoding protease and protease inhibitor, and gene encoding lipase were located upstream and downstream of ABC transporter gene, respectively(see, SEQ ID NO:1). DNA sequence of 8580 bp containing these 6 genes was shown in SEQ ID NO:1, where 292–1725 bp is a region of gene encoding protease PrtA (see: SEQ ID NO:2), 1775–2143 bp, protease inhibitor Inh (see: SEQ ID NO:3), 2215–3951 bp, ABC transporter TliD (see: SEQ ID NO:4), 3992–5293 bp, ABC transporter TliE (see: SEQ ID NO:5), 5296–6741 bp, ABC transporter TliF (see: SEQ ID NO:6) and 6788–8218 bp, thermostable lipase TliA(see: SEQ ID NO:7). From the analysis of DNA sequence, it was found that promoter is located upstream of the ABC transporter gene and transcription terminator is located downstream of lipase gene, which indicates that lipase and ABC transporter genes constitute an operon to produce proteins translated from the same RNA.

EXAMPLE 3
Construction of Transformant Secreting Lipase

A 2.9 kb HindIII-EcoRI-digested fragment containing lipase gene from pJH9 was inserted into pUC19 and named pHOPE' (see: FIG. 1). When this cloned plasmid was expressed in *E. coli* transformed therewith as a control, most of lipase existed in the cell and very small amount of lipase was produced extracellularly($\leq 1$ U/ml). Accordingly, a recombinant vector containing ABC transporter gene was constructed to secrete lipase extracellularly: First of all, 2.3 kb BsrBI-BamHI-digested fragment was isolated from pSCRAP, and ligated into EcoRV/BamHl site of pACYC184 vector to constitute a recombinant vector pBsB-ACYC containing a gene encoding ABC transporter TliD(see: FIG. 1). After the recombinant vector pBsB-ACYC was digested with BamHI and SalI, BamHI-XhoI-digested fragment of pJH9 was inserted to construct a recombinant vector pABC-ACYC containing genes encoding ABC transporter TliD, ABC transporter TliE and ABC transporter TliF(see: FIG. 1). In addition, a transformant was constructed by transforming *E. coli* XL1-Blue with ABC transporter-expressing vector pABC-ACYC. The transformed *E. coli* was named *Escherichia coli* XL1-Blue/pABC-ACYC', and deposited with the Korean Collection for Type Cultures(KCTC, #52, Oun-dong, Yusong-ku, Taejon 305–333, Republic of Korea) an international depository authority, on Mar. 9, 1999 as an accession number of KCTC 0586BP. Then, transformants were prepared by simultaneously transforming two vectors of pABC-ACYC expressing ABC transporter and pHOPE expressing lipase into *E. coli* XL1-Blue, and inoculated in a test tube containing 5 ml LB, and incubated at 25° C. for 2 days. As a result, it was determined that 19 U/ml of lipase was secreted extracellularly. On the contrary, original strain *P. fluorescens* secretes only 1.7 U/ml of lipase when it is incubated for 7 days under the same condition.

EXAMPLE 4
Secretion of Protease by ABC Transporter Gene

Though protease gene located upstream of ABC transporter gene does not constitute an operon with ABC transporter genre, protease secreted extracellularly by the ABC transporter gene was examined as follows: To prepare a recombinant vector containing protease gene located upstream of ABC transporter gene, polymerase chain reaction was carried out by employing a forward primer of 5'-AAGAATTCACTTCTGAAAGTTGCTGGCGT-3' (see;. SEQ ID NO:8) and a reverse primer of 5'-TTAAGCTTGTGGTTTATCTTCCTTGAACC-3' (see: SEQ ID NO:9), respectively, where the former possesses EcoRI recognition site and the latter possesses HindIII recognition site. Amplified PCR product contained protease and protease inhibitor genes. Amplified gene was digested with EcoRI/HindIII and inserted into EcoRI-HindIII-digested pUC18 to give a recombinant vector 'pPROT705' (see: FIG. 1). The recombinant vector 'pPROT705' and pABC-ACYC containing ABC transporter gene were introduced into *E. coli* to construct transformants, and the transformants were incubated at 25° C. to secrete protease to extracellular medium. On the other hand, protease was not detected at all in culture media when only the recombinant vector pPROT705 expressing protease and protease inhibitor was introduced into *E. coli* and incubated.

EXAMPLE 5
Secretion of Lipase by Culturing of Transformants

Figure 2A:
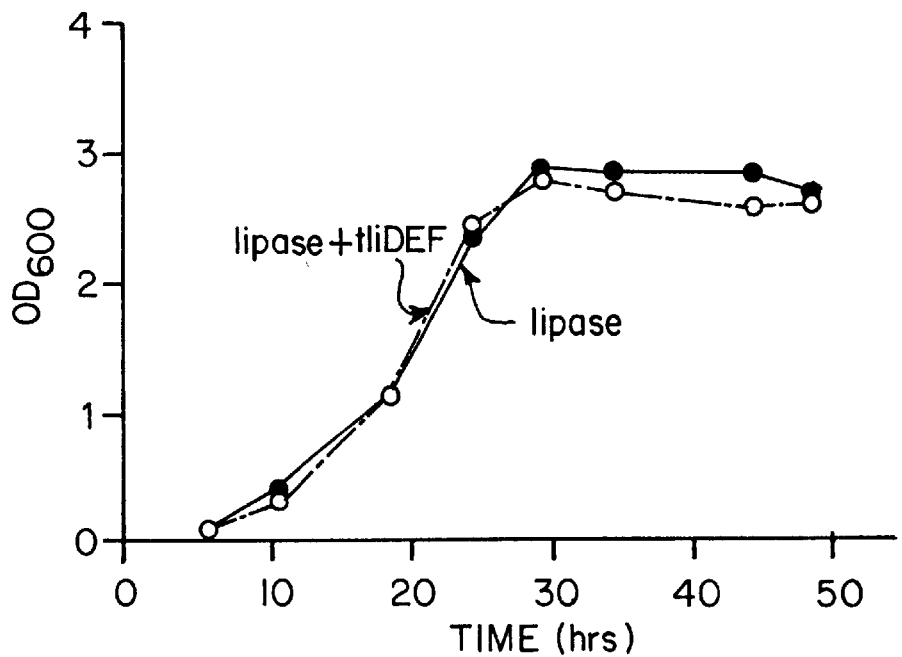
FIG. 2a is a graph showing the changes of $OD_{600}$ value against incubation time of *E. coli* transformants.
Figure 2B:
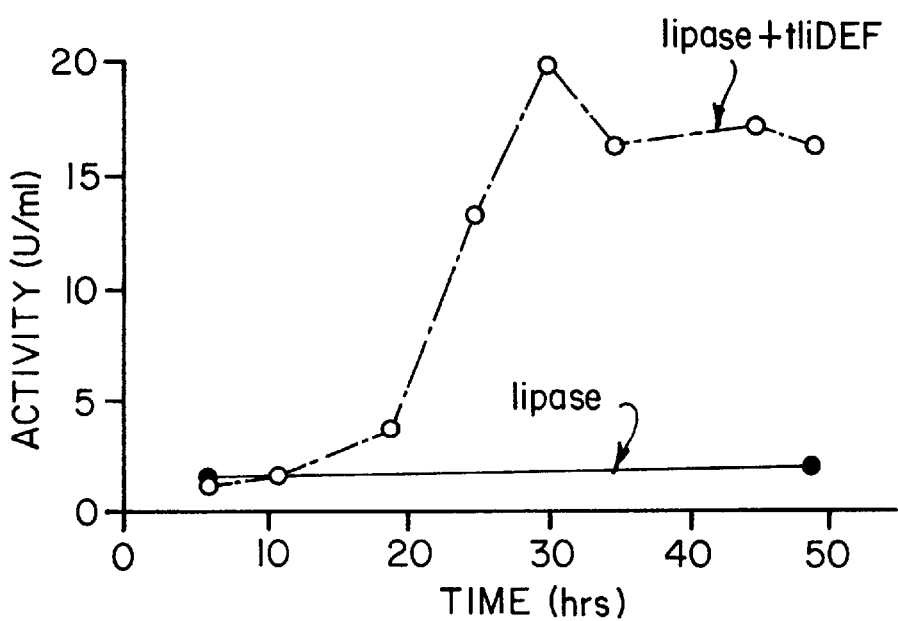
FIG. 2b is a graph showing the changes of lipase activity against incubation time in culture medium.

To confirm whether lipase is secreted extracellularly or not, *E. coli* transformants harboring ABC transporter-expressing vector pABC-ACYC constructed in Example 3 and lipase-expressing vector pHOPE were cultured. As a control, *E. coli* carrying pSTV29 free of ABC transporter gene and lipase-expressing vector pHOPE was incubated under the same condition. And then, activity of lipase secreted extracellularly was examined: 2 transformants were inoculated on LB media, incubated at 25° C. sufficiently, and inoculated again in 100 ml of LB media to reach a concentration of 1% (v/v). When $OD_{600}$ value reached 0.3–0.6, IPTG was added to induce lipase expression and incubated again at 25° C. for about 2 days. Cells were harvested by centrifuging the culture media, and lipase existed in supernatant was assayed by pH-STAT method that titrates fatty acids hydrolyzed from lipid(see: FIGS. 2a and 2b). In FIGS. 2a and 2b,(o) represents *E. coli* carrying ABC transporter-expressing vector pABC-ACYC. constructed in Example 3 and lipase-expressing vector pHOPE; (●), *E. coli* carrying Pstv29 and lipase-expressing vector pHOPE. Changes in $OD_{600}$ value depending on culture time of these transformants and activity of lipase in media were shown in FIGS. 2a and 2b, respectively. Consequently, it was found that a transformant(●) carrying pSTV29 and pHOPE could not secrete lipase extracellularly, while a transformant(o) carrying pABC-ACYC and pHOPE secreted lipase to the extracellular medium.

EXAMPLE 6
Homologous Expression of TliDEFA in *P. fluorescens*

To increase the extracellular production of lipase, the lipase and ABC transporter gene were introduced into *P. fluorescens*. Broad-host-range vector, pDSK519(see: Keen, N. T. et al., Gene, 70(1):191–7(1988)) was used for the construction of pAJH5 containing tliA and pAJH10 containing tliDEFA(see: FIG. 1). The inserts of two plasmids excluded a native promoter upstream of tliD and were under the control of lac promoter of the vectors. *P. fluorescens* harboring pAJH5 or pAJH10 was grown at different temperatures and harvested at the stationary phase when they reached an $OD_{600}$ value of around 2.7. *P. fluorescens* harboring tlia or tliDEFA secreted the lipase only at below 30° C. as was in *E. coli* harboring tliDEFA. These results demonstrated that the ABC transporter was functional at lower temperature in its original host and definitely accountable for higher production of the lipase at lower temperature in P. fluorescens. P. fluorescens harboring pAJH10 secreted much more lipase than E. coli harboring pAJH10 at 25° C. P. fluorescens harboring pAJH5 also secreted the small amount of lipase at 25° C. by chromosomal ABC transporter gene, although no lipase was secreted by E. coli harboring pAJH5.

Much more lipase was secreted by P. fluorescens complemented by ABC transporter and lipase gene than P. fluorescens complemented only by the lipase gene. P. fluorescons secreting lipase with one copy of tliDEF in the chromosome seemed to secrete more lipase by increasing the copy number of tliDEF. In order to investigate the effect of gene dosage, lipase(tliA) and ABC transporter/lipase(tliDEFA) genes were inserted into another broad-host-range vector, pRK415(see: Keen, N. T. et al., Gene, 70(1):191–7(1988)), resulting in pAJH3 and PAJH11, respectively. P. fluorescens carrying the various plasmids and sets of dual plasmids were grown at 25° C. The secreted lipase was detected by the activity and Western blotting of each culture supernatant. P. fluorescens containing dual vector sets(pAJH3 and pAJH10; pAJH11 and pAJH10) secreted more lipase than P. fluorescens containing only one vector indicating that increased gene of ABC transporter and lipase enabled P. fluorescens to secrete more lipase.

EXAMPLE 7

Expression of tliDEFA in Various Pseudomonas sp.

To investigate whether tliA and tliDEF could be expressed in other Pseudomonas, pAJH5 and pAJH10 were introduced by conjugation into various Pseudomonas species; P. aeruginosa, P. fluorescens, P. fragi, P. putida, and P. syringae from Pseudomonas rRNA subgroup I; P. acidovorans (Comamonas acidovorans) from subgroup III. They were all grown in LB at 25° C. for the expression of tliDEF, because tliDEF was functional at below 30° C. P. aeruginosa and E. coli were also grown at 37° C. because they grew too slowly at 25° C. The lipase activity of the culture supernatant of different Pseudomonas species was measured (see: Table 1). When P. fluorescens harboring pAJH10 were grown in LB, they reached around $OD_{600}=2.7$ ±0.2(DCW-1.9 q/L) and secreted the lipase up to 999±70 U/ml which corresponded to 130 μg/ml of lipase based on the protein concentration of culture supernatant and the percentage(74%) of lipase in the supernatant on SDS-PAGE. Recombinant P. fluorescens harboring tliDEFA secreted the lipase 70 times more than P. fluorescens harboring only tliA(14±4 U/ml), while original P. fluorescens secreted no lipase(<1 U/ml) in LB and 2–3 U/ml of lipase in nutrient broth after prolonged incubation at low temperature.

TABLE 1

Secretion of lipase in various recombinant Pseudomonas and E. coli[a]

| Strains | Activity (U/ml) | | |
|---|---|---|---|
| | Original | pAJH5 | pAJH10 |
| E. coli | <1.0 | <1.0 | <1.0 |
| E. coli@25 | <1.0 | <1.0 | 2.9 ± 0.6 |
| P. acidovorans | <1.0 | <1.0 | <1.0 |
| P. aeruginosa | <1.0 | <1.0 | <1.0 |
| P. fluorescens | <1.0 | 14.4 ± 4.8 | 999.3 ± 70.8 |
| P. fragi | <1.0 | <1.0 | 189.5 ± 18.7 |
| P. putida | <1.0 | 18.6 ± 3.0 | 44.4 ± 12.7 |
| P. syringae | <1.0 | 6.3 ± 3.7 | 243.0 ± 42.0 |

[a]P. aeruginosa and E. coli were grown at 37° C., and P. acidovorans, P. fluorescens, P. fragi, P. syringe and E. coli (E. coli@25) were grown at 25° C. in LB medium. The cells were harvested at the stationary phase when they reached an $OD_{600}$ around 2.7.

Other Pseudomonas species carrying no plasmid did not secrete the lipase in LB(<1 U/ml). Recombinant P. syringae and P. putida harboring pAJH5 secreted the lipase, where only tliA was expressed in these strains. It meant that these hosts had inherent ABC transporter for the lipase although there has been no report on the lipase secreted by ABC transporter or ABC transporter itself in these species. Recombinant P. fluorescens, P. fragi, P. syringae, and P. putida secreted much more lipase by the supplemented pAJH10 containing tliDEFA. The ABC transporter was functional in these Pseudomonas species but not functional in P. aeruginosa and P. acidovorans.

It will be apparent to those skilled in the art that certain changes and modifications can be made to this invention without departing from the spirit or scope of the invention as it is set forth herein.

As clearly illustrated and demonstrated above, the present invention provides ABC transporter gene of P. fluorescens encoding a protein which enhances the secretion of foreign proteins extracellularly, a recombinant expression vector containing the transporter gene, a microorganism transformed therewith and a process for preparing foreign proteins which comprises the stops of incubating the transformant, inducing expression of the proteins and leading the proteins to be secreted extracellularly. In accordance with the present invention, foreign proteins can be secreted extracellularly in a simple and efficient manner by employing a secretion system associated with the ABC transporter gene.

What is claimed is:

1. An isolated ATP binding cassette transporter (ABC transporter) from *Psedomonas fluorescens* SIK W1 (KCTC 2689P) which consists of DNA sequence SEQ ID NO: 4, SEQ ID NO: 5 and SEQ ID NO: 6 linked in sequential order.

2. An expression vector which comprises the ABC transporter of claim 1.

3. An expression vector of claim 2, where the expression vector is pACYC184.

4. A recombinant microorganism transformed with the expression vector of claim 3.

5. *Escherichia coli* XL1-Blue which is transformed with the expression vector of claim 3.

6. An expression vector which produces foreign protein, being transformed into a recombinant microorganism together with an expression vector comprising the ABC transporter of claim 1, to secrete foreign protein extracellularly.

7. An expression vector pHOPE which produces lipase, being transformed into a recombinant microorganism together with the expression vector comprising the ABC transporter of claim 1, to secrete lipase extracellularly.

8. An expression vector pPROT705 which produces protease, being transformed into a recombinant microorganism together with the expression vector comprising the ABC transporter of claim 1, to secrete protease extracelluarly.

9. An expression vector comprising a foreign protein gene and the ABC transporter of claim 1, being transformed into a recombinant microorganism, to secrete foreign protein extracelluarly.

10. A microorganism transformed with the expression vector of claim 9.

11. A process for preparing a foreign protein comprising a step of culturing a microorganism transformed with two expression vectors, where the first expression vector comprises foreign protein and the second vector comprises ABC transporter to secrete the foreign protein extracellularly.

12. The process of claim 11 wherein the expression vector for ABC transporter is pACYC184.

13. The process of claim 11 wherein the microorganism is *Escherichia coli*, Pseudomonas sp. , Xanthomonas sp. or Erwinia sp.

14. The process of claim 11 wherein the transformant is cultured at 15–27° C.

15. A process for preparing a foreign protein comprising a step of culturing a microorganism transformed with an expression vector which expresses both foreign protein and ABC transporter, to secrete the foreign protein extracellularly.

16. The process of claim 15 wherein the microorganism is *Escherichia coli*, Pseudomonas sp., Xanthomonas sp. or Erwinia sp.

17. The process of claim 15 wherein the transformant is cultured at 15–27° C.

18. The *Escherichia coli* XL1-Blue of claim 3 which has the Korean Collection for Type Cultures accession number of KCTC 0586BP.

\* \* \* \* \*

SEQUENCE LISTING

<160> NUMBER OF SEQ ID NOS: 9

<210> SEQ ID NO 1
<211> LENGTH: 8580
<212> TYPE: DNA
<213> ORGANISM: Pseudomonas fluorescens -continued

```
<400> SEQUENCE: 1
ggatccatta attaagcagg ccgcccaagt cgtgtcggta ctgctatttt atatttaaat      60
aaccggcgct gtcttttgtc cgacaaaaac tcgccggccc aataaatacg gccttgaact     120
tctgaaagtt gctggcgtgc cactgttttg ccaaagaaat acaagtggac gaaagatttc     180
aagttgtgtc agttttctta cgccttcaaa agaggcgagt gataggacga tctcgcccgc     240
ggggttccta tcgatcaaaa ctgatgcatt tgcaaacaag gaagtacgtt tatgtcaaaa     300
gtaaaagagc aggctattgt gtccgcggcg caagtcagca cggcgtattc gcaaatcgat     360
agcttcagcc atttgtatga ccgtggcggc aacctcacgg tcaatggcaa accgtcctat     420
tccgtcgatc aggtagccac ccagctgctg cgcgacggcc tgcataccg gacgtgaac      480 ggtaacggca agatcgacct gacctacacc ttcctgacct cggcctcctc gagcaccctg     540
aacaaacacg gatctcgggg tttcagccag ttcaacgccc agcagaaaga ccaggcggtg     600
ctggcgatgc aatcctggtc ggacgtggcc aacgtgacct tcactgagaa ggccaccggc     660
ggcgataccc acatgacctt cggcaactac agcggcggcc aggacggcgc ggcggccttc     720
gcctacctgc ccggcaccgg cgcgggctac gacggcacct cgtggtacct gaccaacagc     780
agctacacgc ccaacaagac gccggacctg aacaactacg gccggcagac cctgacccac     840
gaaatcggcc acacccctggg cctggctcac cctggcgact acaacgccgg gaatggcaac     900
ccgacctaca cgacgcgac  ctatggacag gacacgcgcg gctacagcgt catgagttac     960
tggagcgaga gcaacaccaa ccagaacttc agcaaaggcg gggtcgaggc ctatgcgtcg    1020
ggcccgttgc tggacgacat tgcggcgatc cagaagctct acggtgccaa ttacaacacc    1080
cgcgccggcg acaccaccta cggcttcaac tccaacaccg gcgtgatttt ctacagcgcc    1140
acctcgaatg ccgacaagct ggtgttctcg gtgtgggacg gggcggcaa cgataccctg    1200 gacttctccg gttttaccca gaaccagaag atcaacctca atgaggcgtc gttttccgat    1260
gttggcggcc tggtgggcaa cgtgtccatc gccaagggcg tgaccatcga aacgcgttc     1320 ggcggtgccg gcaacgacct gatcatcggc aataacgcgg ccaacgtgat caagggtggc    1380
gccggcaacg acatcatcta cggcggtggc ggtgccgacc aactctgggg cggcgcgggc    1440
aatgacacgt ttgtgttcgg ctccagctcc gactccaagc cgggtgcggc tgacaagatc    1500
tttgacttta cctcgggttc ggacaagatc gacctcagcg gcatcaccaa aggcgcaggc    1560
ctgaccttcg tcaatgcctt caccgggcat gccggcgatg ctgtactgac ctacgcggca    1620
ggcaccaacc tggggaccct ggcggtcgac ttctccggac acggcgtggc ggatttcctc    1680
gtaaccaccg tgggccaggc ggccgtcagc gacatcgtgg cgtgatgcac gagcgcggcg    1740
cttcggcgcc gcgctttgag gatggagccg cttgatgaaa ggttttttc aatcgatcgc    1800 ctgcgctgtg caggtgatag tcgtgtcggc aggagcccac gcaatggcga gcagtcttgt    1860
attacccagc agcgcccaac tggcggggca ctggcagttg caccaggcgg atcaggtctg    1920
cgccctcgat ctgctggaac aggccaacgc cctgggcggc gacgtggcgt gcgtggcgca    1980
atggctgggg gacacgcccc ggacctggtc gccgaccccc gacggcatct ggctgatgaa    2040
cgccgaaggc agcgggataa cccatttgaa tcgccagaaa gaaggcgaat accaggggcg    2100
cacggcgtcc ggtgccatgg tggtattaca ccgcgtgcct tagttgccgt tataacgcta    2160
taacccaagt ttattagttg gccgctcctg atcggggtg cgggcaacta ttgcgtgtcg    2220
tttggttcaa ggaagataaa ccactatggc caagcctatt gccgtggcgc ctttattcaa    2280
```

-continued

| | |
|---|---|
| ggcgtgggtg aatacaagag catcctgatc agtgtcggct gttttaccgc gctgattaac | 2340 |
| ctgttgatgc tggtgccgtc gatttacatg ctgcaagtgt atgaccgcgt gctgtcctcg | 2400 |
| cagaatgaaa ccaccctggt catgttgacg ctgatggtcg tggggttctt tgcgtttatt | 2460 |
| ggcacactgg aagttatccg cagttttatc gtgatccgta ttggcagcca gttggaacgc | 2520 |
| cgtttcaact tgcgcgtgta caaggccgcc tttgaacgca acctgcaacg cggccagggg | 2580 |
| catgccggcc aggcgctggg cgacttgacc ctgttgcgcc agttcatcac cggcccggcg | 2640 |
| ctgttcgcgt ttttcgatgc gccgtggttt cccctctacc tgctggtgat ttcctcttc | 2700 |
| aacgtgtggc tcgggtcct ggccacggcg ggtgcggtgc tgctgatcgg cctggcgtgc | 2760 |
| ctcaacgaat acctgactaa aaagcccttg ggcgaagccg cgccctattc ccagcaatcg | 2820 |
| agccaactgg ccaccagcca tttgcacaac gccgagacca tccaggccat gggcatgctc | 2880 |
| ggtgccctgc gcaaacgctg gtttgccgtg cattcgcaat ttctggggtt gcagaacacc | 2940 |
| gccagcgaca ccggttcggt gatcacgtcc ttgagcaaaa ccctgcgcct gtgcctgcag | 3000 |
| tcactggtgt tgggcctggg cgcattgctg gtgatcaagg gcgatatgac tgccgggatg | 3060 |
| atgatcgcag gctccatcct gatgggccgc gtattgagcc ccatcgacca gttgatcgcg | 3120 |
| gtgtggaaac agtggagttc ggccaagttg gcctaccagc gcctggacga tctgctgcgt | 3180 |
| gaattccctc ccgacagcga gccgatgaaa ctcccggcgc cccacggcca ggtgagcttc | 3240 |
| gagcaggtca gcgcggggcc gcccgggcgg cgcacgccga ccctgcatca ggtcagcttc | 3300 |
| accctgggcg ccggcgaagt cctcggcgtg ctcggtgcct ccggttccgg caaatccacc | 3360 |
| ctggcccgcg tgctggtggg ggtgtggcca accctgggcg gcaccgtgcg cctggatggc | 3420 |
| gccgacatcc atcgctggga ccgcgaagac ctcgcccgc acattggcta tctgccccag | 3480 |
| gacatcgaat tgttcagcgg cagcatcgcc gacaacatcg cgcgttttcg ccaggccgat | 3540 |
| ccggccttgg tcgtgcaggc tgcgcaacag gccggcgtac atgagctgat tctgcggctg | 3600 |
| ccgcacggct acgacacgct gctcggcgac aacggcggcg cctctctgg tgggcagaag | 3660 |
| cagcgggtgg ccctggcccg cgccctgtat ggcgggccgc gcctgatcgt gctggatgag | 3720 |
| cccaactcca acctcgacac cgtcggcgaa gcggccctgg ccagcgccat tgtgcagatg | 3780 |
| aaagcccaag gcagcagcgt ggtactggtc acccatcgct cttcggcatt ggcccaggcc | 3840 |
| gacaaattgc tggtgctcaa cgaaggccgc ctgcagcgtt tggcccgagc caggaggtgt | 3900 |
| tgcgcgcatt gtccggccag ccggaagcac cgaaggaaag gccggtgtg agtttcagtc | 3960 |
| gtcagtatca agcgggaagg aacccaggcg catgagcagt ctcacttttg aacaacgtga | 4020 |
| cgcgcggttc ttcgtgcgca tgggctggtt gctgaccgtg tcggcgccg gtggattttt | 4080 |
| cctctgggcc agcctggcgc cgctggacca gggcattccg gtgcaaggca ccgtcgtggt | 4140 |
| ctcgggcaag cgcaaagcgg tgcaaaacctt cagcccgggc gtggtcagcc ggattctggt | 4200 |
| gcgcgagggc gaaacggtta acaaggcca gccgctgttt cgcctcgacc agacccagaa | 4260 |
| ccaggctgat gtgcagtcgc tgcaagccca gtaccgcctg gctgggcca gcgtggcgcg | 4320 |
| ttggcagagc gagcgcgaca accgttccag catccacttt cccgccgagc tgagcagcaa | 4380 |
| ccccgatccg gccctggccc tggtgctgga aggccacgc caactgttca gcagccgccg | 4440 |
| cgaagccttt gcccgtgagc aggcggggat ccgcgcgaac atcgacggcg ctactgcgca | 4500 |
| actcggcggc atgcgccggg cccgcagcga cctgaccgcc caggcccaat ccctgcgtga | 4560 |
| tcaactgagc aacctgcagc cgctggccga caatggctac atcccgcgca accgcctgat | 4620 |
| ggagtaccag cgccagctgt cccaggtgca gcaggacctg gcgcagaaca ccggtgaaag | 4680 |

-continued

```
cggccgcgtc gagcagggca ttctcgaatc gcgcctgaaa ctgcagcagc acagcgagga    4740
atatcaaaag gaagtgcgca gccaattggc cgacgctcaa ctgcgcagcc tcacgctgga    4800
acagcaactc acctcggccg ggttcgactt gcaacacagt gaaatcaacg cgccggccga    4860
tggtattgcc gtcaacctcg gcgtgcacac cgaaggcgcc gtggtgcgcg ccggtgaaac    4920
cctgttggaa atcgtgcccc agggcacgcg cctggaagtc gaggggcact tgccggtgca    4980
cctggtggac aaggtcggca cgcacctgcc ggtcgacatc ctgttcaccg ccttcaacca    5040
gagccgcaca ccacgcgtgc cggggaggt cagcctgatc tccgccgacc agatgctcga    5100
cgaaaaaacc ggtgcgccgt attacgtgct gcgcaccacg ctcagcgacg cggccgagca    5160
aaaactgcag ggcctggtga tcaagccggg catgccggcc gagatgttcg tgcgcaccgg    5220
cgagcgctcg ctgctcaatt acctgttcaa gccgctgctg gaccgcgccg gctccgcgct    5280
gaccgaggaa tgagcatgag atcgctgctt attgccgtgt tattcagctg cgccagcgct    5340
catgccgcca tgggcccgtt cgacgtctac gagcaggccc tgcgcaacga tccggtgttt    5400
ctcggcgcca tcaaggagcg cgatgccggc ctggagaacc gcaccatcgg ccgcgccggg    5460
ctgctgccca agctgtccta caactacaac aagggccgca caattccca ggccaccttg    5520 cctgacgggc gcggcggcaa ttatcacgac gaccgcaact acaacagtta cggctcgacc    5580
ttcagcctgc agcagccgct gttcgactac gaggcctacg ccaactaccg caaaggcgtg    5640
gcccaggcgt tgttcgctga tgaaagcttt cgcgacaaga gccaggcgct gctggtgcga    5700
gtgctgacct attacaccca ggcgctgttt gcccaggacc agatcgacat cgcccgcgcc    5760
aagaagaagg ccttcgaaca gcagttccag cagaaccggc acctgttcga gcagggcgag    5820
ggcacccgca ccgatattct cgaagccgag tcgcgttatg agctggccac ggccgaggag    5880
atcgaggcgc tggacgagca ggacgccgcc ctgcgcgagc tggggcgtt gatcggagta    5940 cagagcgtca acatcgacga cctggcgccg ctgagtcctg gcttcgccgc cttcagcttg    6000
agcccggcca actacgacac ctggcacgag ctggcgatca gcaataaccc cacgctggca    6060
tcccagcgcc aggccctgga agtggcgcgc tatgaagtgg agcgcaaccg cgccgggcac    6120
ctgccgaaag tcaccgccta tgcgagttcg cgccagcagg agtcggacag cggcaacacc    6180
tacaaccagc gctatgacac caacaccatc ggcgtcgaag tcagcctgcc gttgtatgcc    6240
ggtggcggcg tctcggcgtc cactcgccag gccagccgcg ccatggagca ggccgagtac    6300
gagctggaag gcaagacgcg cgagaccttg atcgaactgc gtcgccaatt cagcgcgtgc    6360
ttgtccgggg tgagcaagtt gcgcgcgtac cagaaggcgc tgacgtcggc cgaagcgttg    6420
gtggtgtcta cccggcaaag catccttggc ggtgagcggg tcaatcttga tgcgttgaat    6480
gccgagcagc agctgtacag cacacgccga gacctggccc aggcgcggta tgactacttg    6540
atggcctgga ccaagctgca ttactacgcc ggcaatttgc gcgacaccga cctggccaag    6600
gtagacgaag ccttcgggac caagagggcc gagcctcccg ctgcagacaa gccccctgtt    6660
gcaaacaaac cgcctgaggc aagccgaccc cctgtggcga gcgggcttgc cccgccttgg    6720
gctgcgcaac aaccccaata aaaccacaca atctccggcc aattccaaca acaagagaga    6780
caagacaatg ggtgtatttg actacaagaa cctcggcacc gaagccagca aaaccttgtt    6840
cgccgatgcc accgcaatca cgttgtatac ctatcacaac ctggataacg gcttcgcagt    6900
cggctaccag caacatggct tggggctcgg cctgccggcc acactggtcg gggcgttgct    6960
cggcagcaca gactcccagg gagtgatccc cggcattccc tggaatcctg actcggaaaa    7020
```

-continued

| | | | |
|---|---|---|---|
| ggccgccctg | gacgcggtgc | acgcagccgg | ttggacgcca atcagcgcca gcgcactggg | 7080 |
| ctacggcggc | aaggtggatg | cgcggggcac | tttttttggc gagaaggccg gctacaccac | 7140 |
| ggcccaggcc | gaagtgctgg | gcaagtacga | tgacgccggc aaactgctcg agatcggcat | 7200 |
| cggttttcgt | ggcacctcgg | gccctcggga | aagcctgatt accgactcca tcggcgatct | 7260 |
| ggtcagcgac | ctgctcgccg | cgctgggccc | caaggactat gcgaaaaact atgccggcga | 7320 |
| agcgtttggc | ggcttgctca | agacggtggc | cgactatgcc ggcgcccatg gcctgagtgg | 7380 |
| caaggatgtg | ctggtcagcg | gccacagcct | gggcggcctg gcggtcaaca gcatggccga | 7440 |
| cctgagcacc | agcaaatggg | cgggtttcta | caaggacgcc aactacctgg cctacgcctc | 7500 |
| gcccacccag | agcgccggcg | ataaggtcct | gaatatcggc tacgaaaacg acccggtatt | 7560 |
| ccgtgcgctg | gacggctcca | ccttcaacct | gtcgtccctc ggcgtgcatg acaaggccca | 7620 |
| cgagtcgacc | accgacaaca | tcgtcagctt | caacgaccac tacgcctcga cgttgtggaa | 7680 |
| tgtgctgccg | ttttccatcg | ccaacctgtc | gacctgggtg tcgcatttgc ccagcgctta | 7740 |
| cggcgacggc | atgacgcgtg | tgctggaatc | ggggttctac gagcaaatga cccgtgactc | 7800 |
| gacgattatc | gtcgccaacc | tgtccgaccc | ggcgcgcgcc aacacctggg tccaggacct | 7860 |
| caaccgcaat | gccgagccgc | acacaggcaa | taccttcatc atcggcagcg acggcaatga | 7920 |
| cctgatccag | ggcggcaagg | gcgcggactt | catcgaaggc ggcaagggca atgacacgat | 7980 |
| ccgcgacaac | agcgggcaca | acaccttttt | gttcagcggg cattttggcc aggatcggat | 8040 |
| tatcggctac | cagccgaccg | acaggctggt | gttccagggc gccgacggca gcaccgacct | 8100 |
| gcgcgaccac | gcgaaggccg | tgggggccga | tacggtgctg agttttggcg ccgactcggt | 8160 |
| gaccctggtc | ggggtcgggc | tggcggcct | gtggagcgag ggtgtgctga tcagttgagg | 8220 |
| agggcgcgac | ggattatcgg | cggttcatgc | gtttaacggt tacctgcgag gtgtatcgcc | 8280 |
| tgttgccgta | cgagggtttg | agcatgtccc | gacttcgatt gttgctgtgt gccgtggtat | 8340 |
| tggggttgag | tgggtgtgcg | gtgtacccgg | cctatccagg cccatgctgc taccgcccgt | 8400 |
| actaccactc | ctactattac | catccttact | atcgcccgta ttactaccat ccgtactacc | 8460 |
| ggtattgatc | ggtcccaaca | aaaagccccg | cattgcgggg cttttcatc tcagtcttcc | 8520 |
| ttgcgcaccg | tggcgacatc | atcggccttg | acccggatgt gcttgccggc aatgtcggtg | 8580 |

<210> SEQ ID NO 2
<211> LENGTH: 1434
<212> TYPE: DNA
<213> ORGANISM: Pseudomonas fluoroscens

<400> SEQUENCE: 2

| | | | |
|---|---|---|---|
| atgtcaaaag | taaagagca | ggctattgtg | tccgcggcgc aagtcagcac ggcgtattcg | 60 |
| caaatcgata | gcttcagcca | tttgtatgac | cgtggcggca acctcacggt caatggcaaa | 120 |
| ccgtcctatt | ccgtcgatca | ggtagccacc | cagctgctgc gcgacggcgc tgcataccgg | 180 |
| gacgtgaacg | gtaacggcaa | gatcgacctg | acctacacct tcctgacctc ggcctcctcg | 240 |
| agcaccctga | caaacacgg | gatctcgggt | ttcagccagt tcaacgccca gcagaaagac | 300 |
| caggcggtgc | tggcgatgca | atcctggtcg | acgtggcca acgtgacctt cactgagaag | 360 |
| gccaccggcg | gcgataccca | catgaccttc | ggcaactaca gcggcggcca ggacggcgcg | 420 |
| gcggccttcg | cctacctgcc | cggcaccggc | gcgggctacg acggcacctc gtggtacctg | 480 |
| accaacagca | gctacacgcc | caacaagacg | ccggacctga caactacgg ccggcagacc | 540 |
| ctgacccacg | aaatcggcca | caccctgggc | ctggctcacc ctggcgacta caacgccggg | 600 |

-continued

```
aatggcaacc cgacctacaa cgacgcgacc tatggacagg acacgcgcgg ctacagcgtc      660
atgagttact ggagcgagag caacaccaac cagaacttca gcaaaggcgg ggtcgaggcc      720
tatgcgtcgg gcccgttgct ggacgacatt gcggcgatcc agaagctcta cggtgccaat      780
tacaacaccc gcgccggcga caccacctac ggcttcaact ccaacaccgg gcgtgatttc      840
tacagcgcca cctcgaatgc cgacaagctg gtgttctcgg tgtgggacgg gggcggcaac      900 gatacccctgg acttctccgg ttttacccag aaccagaaga tcaacctcaa tgaggcgtcg      960
ttttccgatg ttggcggcct ggtgggcaac gtgtccatcg ccaagggcgt gaccatcgag     1020
aacgcgttcg gcggtgccgg caacgacctg atcatcggca ataacgcggc caacgtgatc     1080
aagggtggcg ccggcaacga catcatctac ggcggtggcg gtgccgacca actctggggc     1140
ggcgcgggca atgacacgtt tgtgttcggc tccagctccg actccaagcc gggtgcggct     1200
gacaagatct ttgactttac ctcgggttcg gacaagatcg acctcagcgg catcaccaaa     1260
ggcgcaggcc tgaccttcgt caatgccttc accgggcatg ccggcgatgc tgtactgacc     1320
tacgcggcag gcaccaacct ggggaccctg gcggtcgact tctccggaca cggcgtggcg     1380
gatttcctcg taaccaccgt gggccaggcg gccgtcagcg acatcgtggc gtga          1434
```

<210> SEQ ID NO 3
<211> LENGTH: 369
<212> TYPE: DNA
<213> ORGANISM: Pseudomonas fluoroscens

<400> SEQUENCE: 3

```
atgaaaggtt tttttcaatc gatcgcctgc gctgtgcagg tgatagtcgt gtcggcagga       60
gcccacgcaa tggcgagcag tcttgtatta cccagcagcg cccaactggc ggggcactgg      120
cagttgcacc aggcggatca ggtctgcgcc ctcgatctgc tggaacaggc caacgccctg      180
ggcggcgacg tggcgtgcgt ggcgcaatgg ctgggggaca cgccccggac ctggtcgccg      240
acccccgacg gcatctggct gatgaacgcc gaaggcagcg ggataaccca tttgaatcgc      300
cagaaagaag gcgaatacca ggggcgcacg gcgtccggtg ccatggtggt attacaccgc      360
gtgccttag                                                              369
```

<210> SEQ ID NO 4
<211> LENGTH: 1737
<212> TYPE: DNA
<213> ORGANISM: Pseudomonas fluoroscens

<400> SEQUENCE: 4

```
gtgtcgtttg gttcaaggaa gataaaccac tatggccaag cctattgccg tggcgccttt       60
attcaaggcg tgggtgaata caagagcatc ctgatcagtg tcggctgttt taccgcgctg      120
attaacctgt tgatgctggt gccgtcgatt tacatgctgc aagtgtatga ccgcgtgctg      180
tcctcgcaga tgaaaccacc ctggtcatg ttgacgctga tggtcgtggg gttctttgcg      240
tttattggca cactggaagt tatccgcagt tttatcgtga tccgtattgg cagccagttg      300
gaacgccgtt tcaacttgcg cgtgtacaag gccgcctttg aacgcaacct gcaacgcggc      360 cagggggcatg ccgccaggc gctgggcgac ttgaccctgt tgcgccagtt catcaccggc      420
ccggcgctgt tcgcgttttt cgatgcgccg tggtttcccc tctacctgct ggtgattttc      480
ctcttcaacg tgtggctcgg ggtcctgccc acggcgggtg cggtgctgct gatcggcctg      540
gcgtgcctca acgaatacct gactaaaaag cccttgggcg aagccggcgc ctattcccag      600
```

-continued

```
caatcgagcc aactggccac cagccatttg cacaacgccg agaccatcca ggccatgggc      660
atgctcggtg ccctgcgcaa cgctggtttt gccgtgcatt cgcaatttct ggggttgcag      720
aacaccgcca gcgacaccgg ttcggtgatc acgtccttga gcaaaaccct gcgcctgtgc      780
ctgcagtcac tggtgttggg cctgggcgca ttgctggtga tcaagggcga tatgactgcc      840
gggatgatga tcgcaggctc catcctgatg gccgcgtat tgagcccat cgaccagttg        900 atcgcggtgt ggaaacagtg gagttcggcc aagttggcct accagcgcct ggacgatctg      960
ctgcgtgaat ccctcccga cagcgagccg atgaaactcc cggcgcccca cggccaggtg      1020
agcttcgagc aggtcagcgc ggggccgccc gggcggcgca cgccgaccct gcatcaggtc    1080
agcttcaccc tgggcgccgg cgaagtcctc ggcgtgctcg gtgcctccgg ttccggcaaa    1140
tccaccctgg cccgcgtgct ggtggggggtg tggccaaccc tgggcggcac cgtgcgcctg    1200
gatggcgccg acatccatcg ctgggaccgc gaagacctcg gcccgcacat ggctatctg     1260 ccccaggaca tcgaattgtt cagcggcagc atcgccgaca acatcgcgcg ttttcgccag    1320
gccgatccgg ccttggtcgt gcaggctgcg caacaggccg gcgtacatga gctgattctg    1380
cggctgccgc acggctacga cacgctgctc ggcgacaacg cggcggcct ctctggtggg    1440 cagaagcagc gggtggccct ggcccgcgcc ctgtatggcg ggccgcgcct gatcgtgctg    1500
gatgagccca actccaacct cgacaccgtc ggcgaagcgg ccctggccag cgccattgtg    1560
cagatgaaag cccaaggcag cagcgtggta ctggtcaccc atcgctcttc ggcattggcc    1620
caggccgaca aattgctggt gctcaacgaa ggccgcctgc agcgtttggc ccgagccagg    1680
aggtgttgcg cgcattgtcc ggccagccgg aagcaccgaa ggaaaggccc ggtgtga       1737
```

<210> SEQ ID NO 5
<211> LENGTH: 1302
<212> TYPE: DNA
<213> ORGANISM: Pseudomonas fluoroscens

<400> SEQUENCE: 5

```
atgagcagtc tcacttttga caacgtgac gcgcggttct tcgtgcgcat gggctggttg        60
ctgaccgtgg tcggcgccgg tggattttc ctctgggcca gcctggcgcc gctggaccag      120
ggcattccgg tgcaaggcac cgtcgtggtc tcgggcaagc gcaaagcggt gcaaaccttc      180
agcccgggcg tggtcagccg gattctggtg cgcgagggcg aaacggttaa caaggccag      240 ccgctgtttc gcctcgacca gacccagaac caggctgatg tgcagtcgct gcaagcccag      300
taccgcctgg cctgggccag cgtggcgcgt tggcagagcg agcgcgacaa ccgttccagc      360
atccactttc ccgccgagct gagcagcaac cccgatccgg ccctggccct ggtgctggaa      420
ggccagcgcc aactgttcag cagccgccgc gaagcctttg cccgtgagca ggcggggatc      480
cgcgcgaaca tcgacggcgc tactgcgcaa ctcggcggca tgcgccgggc cgcagcgac      540 ctgaccgccc aggcccaatc cctgcgtgat caactgagca acctgcagcc gctggccgac      600
aatggctaca tcccgcgcaa ccgctgatg gagtaccagc gccagctgtc ccaggtgcag      660
caggacctgg cgcagaacac cggtgaaagc ggccgcgtcg agcagggcat tctcgaatcg      720
cgcctgaaac tgcagcagca cagcgaggaa tatcaaaagg aagtgcgcag ccaattggcc      780
gacgctcaac tgcgcagcct cacgctggaa cagcaactca cctcggccgg gttcgacttg      840
caacacagtg aaatcaacgc gccggccgat ggtattgccg tcaacctcgg cgtgcacacc      900
gaaggcgccg tggtgcgcgc cggtgaaacc ctgttgaaa tcgtgcccca gggcacgcgc      960
ctggaagtcg aggggcactt gccggtgcac ctggtggaca aggtcggcac gcacctgccg    1020
```

-continued

```
gtcgacatcc tgttcaccgc cttcaaccag agccgcacac cacgcgtgcc gggggaggtc       1080
agcctgatct ccgccgacca gatgctcgac gaaaaaaccg gtgcgccgta ttacgtgctg       1140
cgcaccacgc tcagcgacgc ggccgagcaa aaactgcagg gcctggtgat caagcccggc       1200
atgccggccg agatgttcgt gcgcaccggc gagcgctcgc tgctcaatta cctgttcaag       1260
ccgctgctgg accgcgccgg ctccgcgctg accgaggaat ga                         1302
```

<210> SEQ ID NO 6
<211> LENGTH: 1446
<212> TYPE: DNA
<213> ORGANISM: Pseudomonas fluoroscens

<400> SEQUENCE: 6

```
atgagatcgc tgcttattgc cgtgttattc agctgcgcca gcgctcatgc cgccatgggc        60
ccgttcgacg tctacgagca ggccctgcgc aacgatccgg tgtttctcgg cgccatcaag       120
gagcgcgatg ccggcctgga gaaccgcacc atcgccgcg ccgggctgct gcccaagctg       180
tcctacaact acaacaaggg ccgcaacaat tcccaggcca ccttgcctga cgggcgcggc       240
ggcaattatc acgacgaccg caactacaac agttacggct cgaccttcag cctgcagcag       300
ccgctgttcg actacgaggc ctacgccaac taccgcaaag gcgtggccca ggcgttgttc       360
gctgatgaaa gctttcgcga caagagccag gcgctgctgg tgcgagtgct gacctattac       420
acccaggcgc tgtttgccca ggaccagatc gacatcgccc gcgccaagaa gaaggccttc       480
gaacagcagt tccagcagaa ccggcacctg ttcgagcagg gcgagggcac ccgcaccgat       540
attctcgaag ccgagtcgcg ttatgagctg gccacggccg aggagatcga ggcgctggac       600
gagcaggacg ccgccctgcg cgagctgggg gcgttgatcg gagtacagag cgtcaacatc       660
gacgacctgg cgccgctgag tcctggcttc gccgccttca gcttgagccc ggccaactac       720
gacacctggc acgagctggc gatcagcaat aaccccacgc tggcatccca gcgccaggcc       780
ctggaagtgg cgcgctatga agtggagcgc aaccgcgccg gcacctgcc gaaagtcacc       840 gcctatgcga gttcgcgcca gcaggagtcg gacagcggca acacctacaa ccagcgctat       900
gacaccaaca ccatcggcgt cgaagtcagc ctgccgttgt atgccggtgg cggcgtctcg       960
gcgtccactc gccaggccag ccgcgccatg gagcaggccg agtacgagct ggaaggcaag      1020
acgcgcgaga ccttgatcga actgcgtcgc caattcagcg cgtgcttgtc cggggtgagc      1080
aagttgcgcg cgtaccagaa ggcgctgacg tcggccgaag cgttggtggt gtctacccgg      1140
caaagcatcc ttggcggtga gcgggtcaat cttgatgcgt tgaatgccga gcagcagctg      1200
tacagcacac gccgagacct ggcccaggcg cggtatgact acttgatggc ctggaccaag      1260
ctgcattact acgccggcaa tttgcgcgac accgacctgg ccaaggtaga cgaagccttc      1320
gggaccaaga gggccgagcc tcccgctgca gacaagcccc tgttgcaaa caaaccgcct      1380 gaggcaagcc gaccccctgt ggcgagcggg cttgccccgc cttgggctgc gcaacaaccc      1440
caataa                                                                1446
```

<210> SEQ ID NO 7
<211> LENGTH: 1431
<212> TYPE: DNA
<213> ORGANISM: Pseudomonas fluoroscens

<400> SEQUENCE: 7

```
atgggtgtat ttgactacaa gaacctcggc accgaagcca gcaaaacctt gttcgccgat        60
```

-continued

```
gccaccgcaa tcacgttgta tacctatcac aacctggata acggcttcgc agtcggctac      120
cagcaacatg gcttggggct cggcctgccg gccacactgg tcgggcgtt gctcggcagc       180 acagactccc agggagtgat ccccggcatt ccctggaatc ctgactcgga aaaggccgcc      240
ctggacgcgg tgcacgcagc cggttggacg ccaatcagcg ccagcgcact gggctacggc     300
ggcaaggtgg atgcgcgggg cacttttttt ggcgagaagg ccggctacac cacggcccag    360
gccgaagtgc tgggcaagta cgatgacgcc ggcaaactgc tcgagatcgg catcggtttt    420
cgtggcacct cgggccctcg ggaaagcctg attaccgact ccatcggcga tctggtcagc    480
gacctgctcg ccgcgctggg ccccaaggac tatgcgaaaa actatgccgg cgaagcgttt   540
ggcggcttgc tcaagacggt ggccgactat gccggcgccc atggcctgag tggcaaggat   600
gtgctggtca gcggccacag cctgggcggc ctggcggtca acagcatggc cgacctgagc  660
accagcaaat gggcgggttt ctacaaggac gccaactacc tggcctacgc ctcgcccacc   720
cagagcgccg gcgataaggt cctgaatatc ggctacgaaa acgacccggt attccgtgcg   780
ctggacggct ccaccttcaa cctgtcgtcc ctcggcgtgc atgacaaggc ccacgagtcg   840
accaccgaca acatcgtcag cttcaacgac cactacgcct cgacgttgtg gaatgtgctg   900
ccgttttcca tcgccaacct gtcgacctgg gtgtcgcatt tgcccagcgc ttacggcgac  960
ggcatgacgc gtgtgctgga atcggggttc tacgagcaaa tgacccgtga ctcgacgatt  1020
atcgtcgcca acctgtccga cccggcgcgc gccaacacct gggtccagga cctcaaccgc  1080
aatgccgagc cgcacacagg caataccttc atcatcggca gcgacggcaa tgacctgatc  1140
cagggcggca agggcgcgga cttcatcgaa ggcggcaagg gcaatgacac gatccgcgac  1200
aacagcgggc acaacacctt tttgttcagc gggcattttg gccaggatcg gattatcggc  1260
taccagccga ccgacaggct ggtgttccag ggcgccgacg gcagcaccga cctgcgcgac  1320
cacgcgaagg ccgtgggggc cgatacggtg ctgagttttg gcgccgactc ggtgaccctg  1380
gtcggggtcg ggctgggcgg cctgtggagc gagggtgtgc tgatcagttg a              1431
```

<210> SEQ ID NO 8
<211> LENGTH: 29
<212> TYPE: DNA
<213> ORGANISM: Artificial Sequence
<220> FEATURE:
<223> OTHER INFORMATION: Single stranded oligonucleotide primer

<400> SEQUENCE: 8
aagaattcac ttctgaaagt tgctggcgt                                          29

<210> SEQ ID NO 9
<211> LENGTH: 29
<212> TYPE: DNA
<213> ORGANISM: Artificial Sequence
<220> FEATURE:
<223> OTHER INFORMATION: Single stranded oligonucleotide primer

<400> SEQUENCE: 9
ttaagcttgt ggtttatctt ccttgaacc                                          29